United States Patent
Petralia et al.

(10) Patent No.: US 10,124,105 B2
(45) Date of Patent: Nov. 13, 2018

(54) DEVICE FOR THE EXTRACORPOREAL OXYGENATION OF THE BLOOD OF A PATIENT

(71) Applicant: EUROSETS S.R.L., Medolla (IT)

(72) Inventors: Antonio Petralia, Lugo (IT); Nicola Ghelli, S. Pietro in Casale (IT); Edgardo Costa, Medolla (IT); Roberto Balanzoni, Medolla (IT)

(73) Assignee: Eurosets S.r.l., Medolla (IT)

( * ) Notice: Subject to any disclaimer, the term of this patent is extended or adjusted under 35 U.S.C. 154(b) by 299 days.

(21) Appl. No.: 15/112,769

(22) PCT Filed: Jan. 16, 2015

(86) PCT No.: PCT/IB2015/050334
§ 371 (c)(1),
(2) Date: Jul. 20, 2016

(87) PCT Pub. No.: WO2015/107486
PCT Pub. Date: Jul. 23, 2015

(65) Prior Publication Data
US 2016/0339163 A1    Nov. 24, 2016

(30) Foreign Application Priority Data

Jan. 20, 2014   (IT) .............. MO2014A0010

(51) Int. Cl.
*A61M 1/00*   (2006.01)
*A61M 1/16*   (2006.01)
*A61M 1/36*   (2006.01)

(52) U.S. Cl.
CPC ........ *A61M 1/1698* (2013.01); *A61M 1/1629* (2014.02); *A61M 1/1631* (2014.02); *A61M 1/3627* (2013.01); *A61M 2207/00* (2013.01)

(58) Field of Classification Search
CPC .............. A61M 1/1698; A61M 1/1629; A61M 1/1631; A61M 1/3627; A61M 2207/00
(Continued)

(56) References Cited

U.S. PATENT DOCUMENTS 6,113,782 A * 9/2000 Leonard ............... B01D 63/022
                                                               210/321.89
2010/0269342 A1  10/2010 Carpenter
(Continued)

FOREIGN PATENT DOCUMENTS

EP    1618906 A1    1/2006
EP    1834656 A1    9/2007
(Continued)

OTHER PUBLICATIONS

European Search Report dated Sep. 23, 2014 from Italian Patent Application No. MO20140010, filed Jan. 20, 2014.
(Continued)

*Primary Examiner* — Philip R Wiest
(74) *Attorney, Agent, or Firm* — Sunstone IP

(57) ABSTRACT

A device (1) for the extracorporeal oxygenation of the blood of a patient, comprising a containment casing (2) which has at least an inlet port (4) of the venous blood and at least an outlet port (5) of the arterial blood, at least an inlet channel (6) and at least an outlet channel (7) of a work gas intended to provide oxygen to blood and/or to remove $CO_2$ from the same, at least a bundle of hollow fibers (8) arranged within the casing (2) and placed between the inlet channel (6) and the outlet channel (7), the hollow fibers being in communication with the inlet and outlet channels (6, 7) and being intended to be crossed by the relative work gas, at least a first and at least a second filtering elements (12, 13) arranged inside the bundle of hollow fibers (8) and spaced apart the one from the other, the filtering elements (12, 13) being able
(Continued)

to trap any air bubbles present in the treated blood, where the first and second filtering elements (12, 13) define a relative open profile and where the hollow fibers (8) cross the first and second filtering elements (12, 13) uninterruptedly.

16 Claims, 3 Drawing Sheets

(58) Field of Classification Search
USPC .................................................. 422/44–48
See application file for complete search history.

(56) References Cited

U.S. PATENT DOCUMENTS

| | | |
|---|---|---|
| 2010/0274170 A1 | 10/2010 | Carpenter |
| 2011/0186514 A1* | 8/2011 | Ogihara .............. A61M 1/1698 210/639 |

FOREIGN PATENT DOCUMENTS

| | | |
|---|---|---|
| WO | 99/47189 A1 | 9/1999 |
| WO | 2012/133372 A1 | 10/2012 |

OTHER PUBLICATIONS

International Search Report dated Jan. 10, 2015 from International Patent Application No. PCT/IB2015/050334 filed Jan. 16, 2015.

* cited by examiner

DEVICE FOR THE EXTRACORPOREAL OXYGENATION OF THE BLOOD OF A PATIENT

TECHNICAL FIELD

The present invention relates to a device for the extracorporeal oxygenation of the blood of a patient.

BACKGROUND ART

As is known, in extracorporeal blood circulation effected to bypass the patient's heart and lungs during cardiac arrest and open heart surgical operations, or else to temporarily help the patient's circulation and breathing in clinical conditions of acute cardiac insufficiency and/or breathing insufficiency (ECMO), blood oxygenation devices are used which are suitable for enriching the blood with oxygen and replacing, from a functional viewpoint, the patient's lungs.

The blood oxygenation devices of known type, commonly called "oxygenators", are made up of a casing having an inlet fitting for the venous blood and an outlet fitting for the arterial blood, inside which a work gas is conveyed suitable for yielding oxygen to the blood and for receiving carbon dioxide from it.

A particular type of known oxygenator is the "hollow fibre" type, i.e., characterized by a bundle of hollow fibres arranged inside the oxygenator body and made up of a material semi-permeable to the gases but not to liquids. These hollow fibres are therefore crossed internally by the work gas and are washed on the outside by the blood coming from the patient.

The known oxygenators therefore also comprise an inlet channel and an outlet channel for the work gas, where the entering gas consists of oxygen, if necessary mixed with air, and the escaping gas consists of oxygen and carbon dioxide.

Because, generally, the blood that crosses the oxygenator contains air bubbles, it is best for such air bubbles to be removed before the blood itself is reintroduced into the patient.

The patent EP 1834656 describes an integrated device for heating and oxygenating the blood, which envisages a fitting for removing air bubbles in the blood, arranged above the blood outlet fitting itself, through which any air bubbles in the blood are conveyed.

The device described by EP 1834656 has a number of drawbacks, inasmuch as it does not ensure that the bubbles in the blood are actually removed and not therefore dragged by the flow of blood which is reintroduced into the patient.

DESCRIPTION OF THE INVENTION

The main aim of the present invention is to provide a device for the extracorporeal oxygenation of the blood which allows to considerably reduce, compared to the devices of known type, the risk that the air bubbles present in the blood to be treated are reintroduced into the patient.

Within this aim, one object of the present invention is to provide a device for the oxygenation of the blood which is able at the same time to achieve efficient filtration of the air bubbles present in the blood itself.

One object of the present invention is to provide a device for the oxygenation of the blood which is of small dimensions.

Another object of the present invention is to provide a device for the extracorporeal oxygenation of the blood which allows to overcome the mentioned drawbacks of the prior art within the ambit of a simple, rational, easy and effective to use as well as low cost solution.

The above mentioned objects are achieved by the present device for the extracorporeal oxygenation of the blood of a patient according to claim 1.

BRIEF DESCRIPTION OF THE DRAWINGS

Other characteristics and advantages of the present invention will become better evident from the description of a preferred but not exclusive embodiment of a device for the extracorporeal oxygenation of the blood, illustrated by way of an indicative, but not limitative example in the accompanying drawings in which.

EMBODIMENTS OF THE INVENTION

Figure 1:
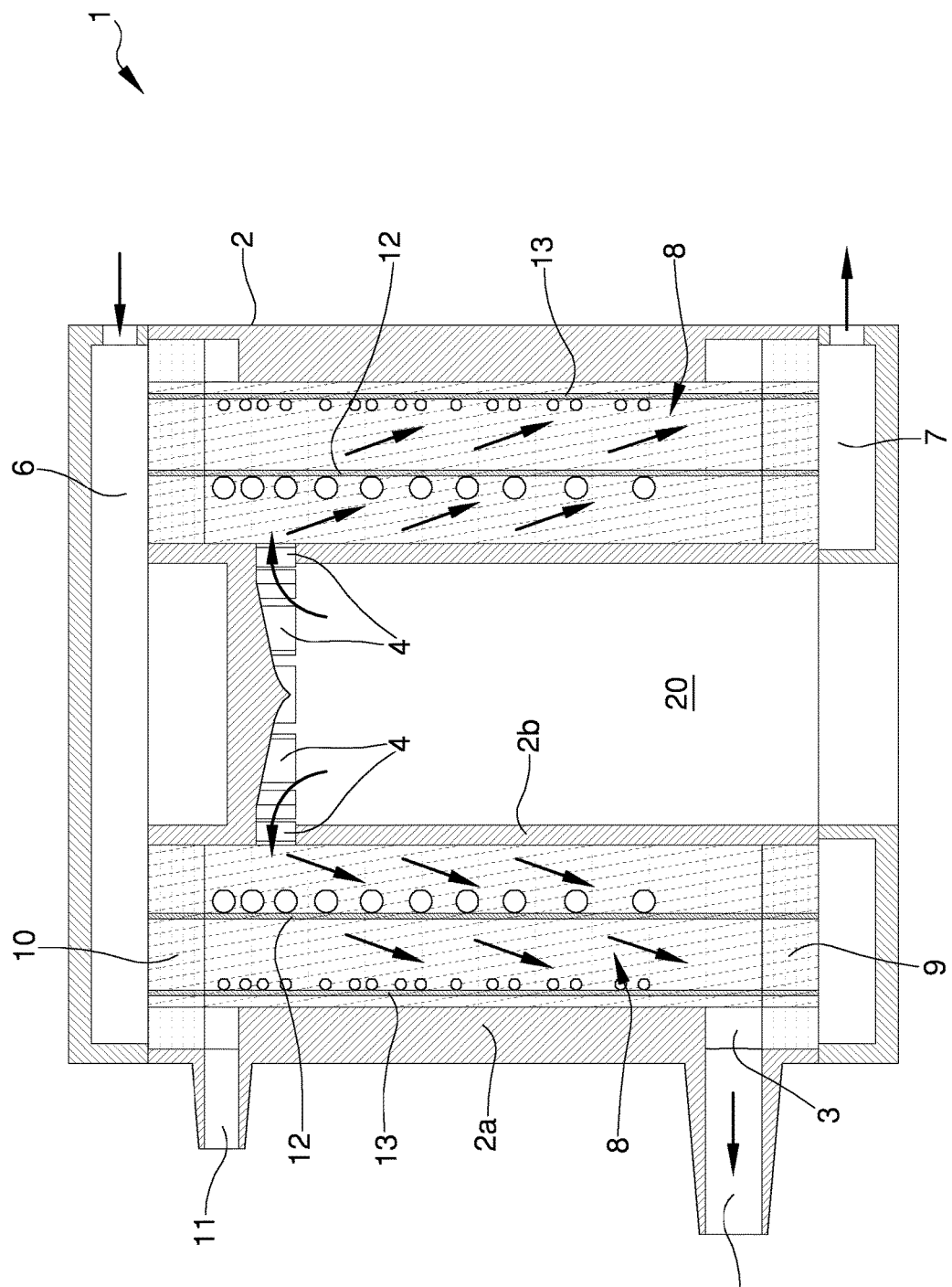
FIG. 1 is a longitudinal sectional view of a device for the oxygenation according to the invention in a first embodiment.

With particular reference to these illustrations, a device for the extracorporeal oxygenation of the blood is globally indicated by reference number 1.

The device 1 comprises a casing 2 that defines an oxygenation chamber 3 inside which the oxygenation occurs of the blood coming from the patient.

The casing 2 has an inlet port 4 which receives the blood to be oxygenated coming from the patient (called venous blood), and an outlet port 5, through which the oxygenated blood (called arterial blood), and which is to be subsequently reintroduced into the patient, comes out.

Both the inlet port 4 and the outlet port 5 face onto the oxygenation chamber 3.

The inlet port 4 can be connected to other devices, not shown in the illustrations, such as a supply pump suitable for keeping the blood in circulation, e.g., a roller pump, and a thermal conditioning device suitable for keeping the blood temperature under control by adding or subtracting heat, e.g., a heat exchanger.

The casing 2 also has an inlet channel 6 and an outlet channel 7 for a work gas, generally oxygen or oxygen mixed with air, suitable for yielding oxygen to the blood and removing $CO_2$ from it.

Inside the device 1, and more in particular inside the casing 2, means of transit 8 are arranged for the transit of the work gas.

The means of transit 8 are made up of at least a bundle of hollow fibres semi-permeable to gas, placed between the inlet channel 6 and the outlet channel 7 and communicating with these. The hollow fibres are therefore crossed internally by oxygen and washed on the outside by the blood.

It therefore follows that the inlet channel 6 is crossed by oxygen, if necessary mixed with air, and the outlet channel 7 is crossed by oxygen and carbon dioxide.

More in particular, the extremities of the hollow fibres are drowned in rings of polyurethane resin 9 and 10, called "potting", and are open towards the inlet channel 6 and the outlet channel 7, respectively. The device 1 thus has a lower potting 9 and an upper potting 10.

During the operation of the device 1, the blood therefore exchanges oxygen and carbon dioxide with the gas that circulates inside the hollow fibres.

In the particular embodiment shown in the illustrations, the casing 2 has at least an outer containment wall 2a, which delimits its overall dimensions, and at least an inner wall 2b which defines a substantially cylindrical seat 20 for housing a heat exchanger (not shown in the illustrations).

The oxygenation chamber 3 is therefore defined by the volume placed between the outer wall 2a and the inner wall 2b, has a substantially annular conformation and inside it is arranged the bundle of hollow fibres 8.

Figure 2:
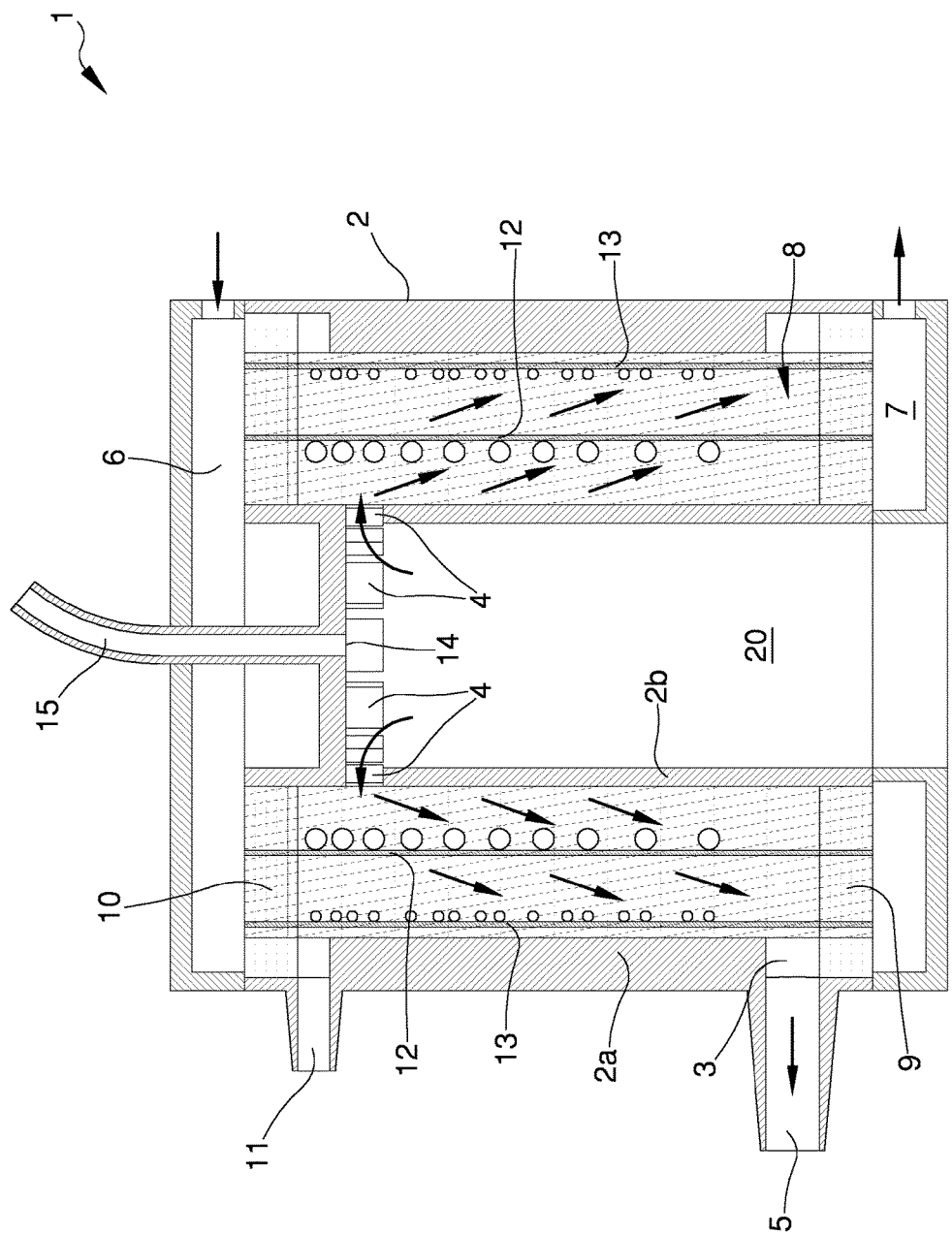
FIG. 2 is a longitudinal sectional view of a device for the oxygenation according to the invention in a second embodiment.

As shown in FIGS. 1 and 2, the inner wall 2b defines a plurality of consecutive and coplanar inlet ports 4 facing onto the oxygenation chamber 3, and the outer wall 2a defines the outlet port 5 of the oxygenated blood, as well as a further port 11 for the escape of any air bubbles in the blood itself.

The device 1 comprises at least a first and at least a second filtering element suitable for trapping any air bubbles in the blood and identified in the figures with reference numbers 12 and 13 respectively.

The first and the second filtering elements 12 and 13 are arranged inside the bundle of hollow fibres 8 and are spaced apart the one from the other.

More in particular, the first and the second filtering elements 12 and 13 are arranged along the thickness of the bundle of hollow fibres 8 and are therefore placed between the hollow fibres themselves.

According to the invention, the first and the second filtering elements 12 and 13 define a relative open profile and the hollow fibres 8, which are arranged both inside and outside the open profiles defined by the filtering elements themselves, cross the first and the second filtering elements 12 and 13 seamlessly.

Figure 3:
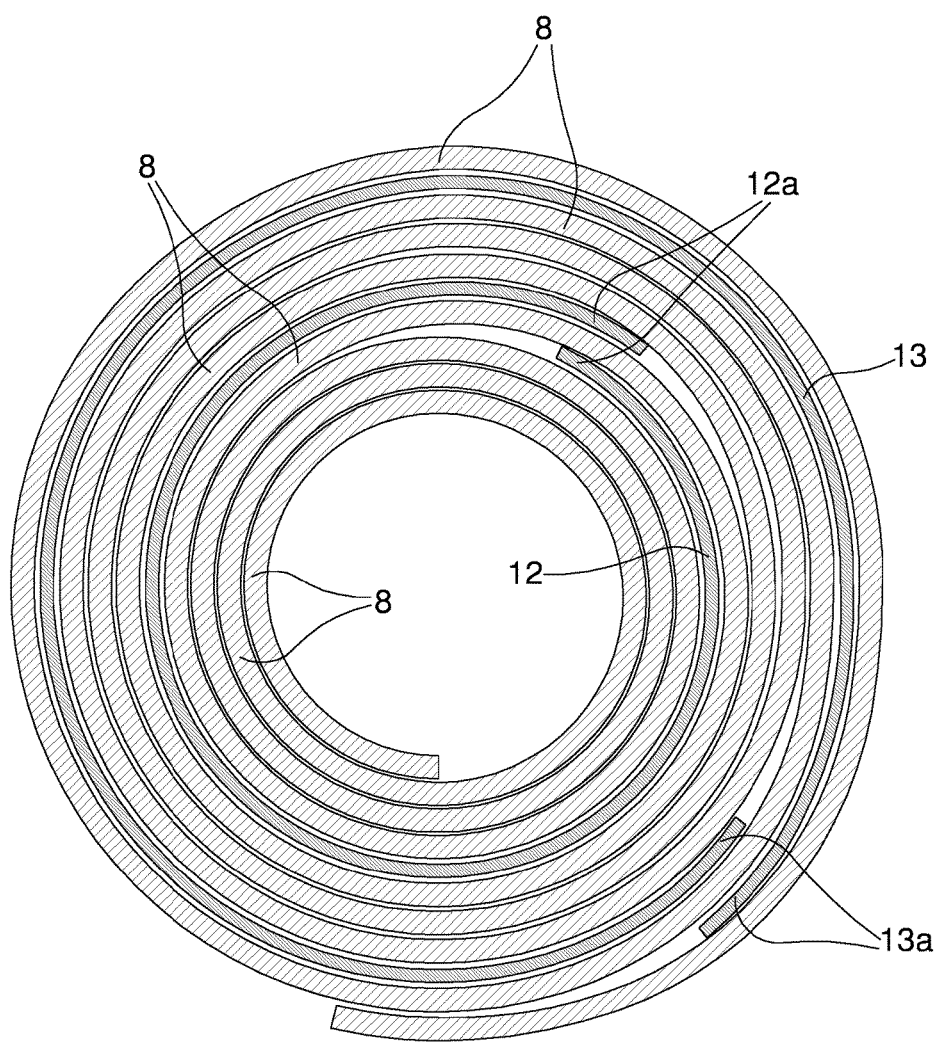
FIG. 3 is a diagrammatic cross-section of the bundle of hollow fibres and of the filtering elements contained within the device of FIG. 1.

As shown in FIG. 3, the first and the second filtering elements 12 and 13 each have two relative flaps 12a, 13a, which are spaced apart the one from the other to define the above-mentioned open profile. More in detail, the flaps 12a and 13a define a gap through which the hollow fibres 8 pass (shown schematically in FIG. 3).

Suitably, the flaps 12a and 13a correspond to the extremity portions of the filtering elements 12 and 13.

In the embodiment shown in FIG. 3, the flaps 12a and the flaps 13a are superimposed on one another.

Advantageously, the hollow fibres 8 are arranged around the filtering elements 12 and 13. More in particular, the hollow fibres 8 are arranged in such a way as to substantially follow both the inner profile and the outer profile of the filtering elements 12 and 13.

As shown in FIG. 3, the hollow fibres 8 are rolled up, passing through the gap positioned between the flaps 12a and 13a, to define a sort of spiral.

More in detail, the hollow fibres 8 are shaped like a flexible sheet rolled up to define the above-mentioned bundle of hollow fibres and the filtering elements 12, 13 are of the plate-shaped type, are also of the flexible type and are arranged along the coils of such flexible sheet.

In a preferred embodiment, the flexible sheet of hollow fibres 8 has two superimposed layers and the filtering elements 12, 13 are placed between such layers.

To make the device 1, the first and second filtering elements 12, 13 are arranged spaced apart the one from the other along the flexible sheet of hollow fibres 8, which is then rolled up to define a bundle of hollow fibres 8.

Following such rolling up, the first and the second filtering elements 12, 13 are positioned between the coils of the flexible sheet.

Subsequently, the bundle of hollow fibres 8 thus obtained is inserted within the casing 2 and the casing itself is closed.

Advantageously, the first and the second filtering elements 12 and 13 are arranged in succession the one to the other proceeding from the inside towards the outside of the casing 2. The first filtering element 12 is therefore that positioned innermost, i.e., the one closest to the inner wall 2b, while the second filtering element 13 is that closest to the outer wall 2a of the casing 2.

Advantageously, the first filtering element 12 has a greater filtering capacity than that of the second filtering element 13.

By "filtering capacity", as used in the present description, is meant the quantity of fluid that crosses the filtering element before this becomes blocked. The lower the filtering speed and the filtering capacity, the more time is needed to perform the filtering operation.

It follows therefore that, the greater the filtering capacity, the greater are the dimensions of the particles, and therefore of the air bubbles in this case, which are allowed to pass by the relative filtering element.

Suitably, the filtering elements 12 and 13 are of the mesh or net type, i.e., they have a plurality of openings, where the openings of the first filtering element 12 have larger dimensions than the openings of the second filtering element 13.

The openings of the first filtering element 12 have dimensions between 70 μm and 90 μm, preferably equal to around 80 μm.

The openings of the second filtering element 13 instead have dimensions between 30 μm and 50 μm, preferably equal to around 40 μm.

Both the filtering elements 12 and 13 extend along the entire longitudinal extension of the bundle of hollow fibres 8.

More in detail, the filtering elements 12 and 13 extend from the lower potting 9 as far as the upper potting 10.

For a technician in the sector, it is easy to appreciate how the device 1 can, in a further embodiment, comprise further filtering elements placed in between the bundle of hollow fibres 8 in order to make the filtering of the air bubbles present in the blood even more effective.

In the second embodiment shown in FIG. 2, the casing 2 also has an outlet mouth 14 for the bubbles contained in the venous blood which is arranged upstream of the inlet port 4 with respect to the direction of the flow of blood towards the outlet port 5.

In other words, the outlet mouth 14 is arranged upstream of the oxygenation chamber 3 in such a way that it is intercepted by the blood before this enters the oxygenation chamber itself.

More in particular, the outlet mouth 14 is defined at the wall that delimits the seat 20 at the top and is placed in communication with the outside by means of a pipe 15.

As shown in FIG. 2, the pipe 15 crosses the inlet channel 6.

The operation of the present invention is the following.

The venous blood coming from the patient enters the device 1, e.g., by means of the heat exchanger insertable within the seat 20 and not shown in the illustrations, and enters the oxygenation chamber 3 passing through the inlet ports 4.

In the embodiment shown in FIG. 2, a portion of the venous blood coming out of the heat exchanger inserted within the seat 20 inasmuch as lighter, and in particular that containing the bubbles of larger dimensions, enters the pipe 15 through the outlet mouth 14 before entering the oxygenation chamber 3.

At the same time, the work gas is conveyed inside the inlet channel 6, passes through the bundle of hollow fibres 8 and exits along the outlet channel 7 after the gaseous exchange with the blood which occurs inside the oxygenation chamber 3.

Inside the oxygenation chamber 3, the blood washes the hollow fibres on the outside and, as discussed above, yields carbon dioxide and becomes enriched with oxygen.

At the same time, the blood that crosses the oxygenation chamber 3 crosses the first and the second filtering elements 12 and 13 in succession, thus undergoing cascade filtration.

More in detail, the blood undergoes a first filtration by the first filtering element 12, by effect of which the air bubbles of larger dimensions are trapped and, subsequently, a second filtration by the second filtering element 13, by effect of which the air bubbles of smaller dimensions which have passed through the first filtering element 12 are trapped.

The blood thus undergoes multiple filtration during the crossing of the bundle of hollow fibres 8, so that the flow that exits from the outlet port 5 is substantially devoid of air bubbles.

The oxygenated and filtered blood therefore exits from the device 1 through the outlet port 5 and the work gas, after yielding oxygen to the blood and being enriched with carbon dioxide, reaches the outlet channel 7.

It has in practice been ascertained how the described invention achieves the proposed objects and in particular the fact is underlined that the device according to the invention permits successfully trapping the air bubbles present in the blood coming from the patient at the same time as his/her oxygenation.

Again, the presence of two or more filtering elements arranged in succession the one to the other and having a gradually decreasing filtering capacity, permits optimizing the trapping of air bubbles and achieving a degree of filtration not otherwise achievable by means of the use of a single filtering element.

The invention claimed is:

1. Device for the extracorporeal oxygenation of the blood of a patient, comprising:
    a containment casing which has at least an inlet port of the venous blood and at least an outlet port of the arterial blood, at least an inlet channel and at least an outlet channel of a work gas intended to provide oxygen to blood and/or to remove $CO_2$ from the same;
    at least a bundle of hollow fibres arranged within said casing and placed between said inlet channel and said outlet channel, said hollow fibres being in communication with said inlet and outlet channels and being intended to be crossed by the relative work gas;
    at least a first and at least a second filtering elements arranged inside said bundle of hollow fibres and spaced apart the one from the other, said filtering elements being able to trap any air bubbles present in the treated blood
    and wherein said first and second filtering elements define a relative open profile and that said hollow fibres cross said first and second filtering elements uninterruptedly.

2. The device according to claim 1, wherein said first and second filtering elements each have two relative flaps which are spaced apart the one from the other to define a gap and by the fact that said hollow fibres are arranged inside and outside the open profile defined by the filtering elements themselves and are inserted through said gap.

3. The device according to claim 2, wherein said flaps correspond to the extremity portions of said filtering elements.

4. The device according to claim 1, wherein said hollow fibres are arranged around said filtering elements and substantially follow the inner profile and the outer profile thereof.

5. The device according to claim 1, wherein said hollow fibres are shaped like a flexible sheet rolled up to define said bundle of hollow fibres, said filtering elements being of the plate-shaped type and being arranged along the coils of said flexible sheet.

6. The device according to claim 5, wherein said flexible sheet has two superimposed layers and that said filtering elements are placed between said layers.

7. The device according to claim 1, wherein said first and second filtering elements are arranged in succession the one to the other proceeding from the inside towards the outside of said casing.

8. The device according to claim 7, wherein said first and second filtering elements have a substantially annular conformation, said first filtering element being arranged inside said second filtering element.

9. The device according to claim 1, wherein said first filtering element has a greater filtering capacity than that of said second filtering element.

10. The device according to claim 9, wherein said first and second filtering elements are of the mesh type, the openings of said first filtering element having larger dimensions than those of said second filtering element.

11. The device according to claim 10, wherein the openings of said first filtering element have dimensions between 70 μm and 90 μm.

12. The device according to claim 10, wherein the openings of said second filtering element have dimensions between 30 μm and 50 μm.

13. The device according to claim 1, wherein said casing defines at least an outlet mouth for the bubbles contained in the venous blood which is arranged upstream of said inlet port with respect to the direction of the flow of venous blood towards said outlet port.

14. The device according to claim 13, wherein said casing defines at least a seat for housing a heat exchanger and by the fact that said outlet mouth is defined at the wall that delimits said seat at the top.

15. The device according to claim 13, wherein said outlet mouth is placed in communication with the outside by means of a pipe which crosses said inlet channel.

16. A method for the manufacture of a device for the extracorporeal oxygenation of the blood of a patient, wherein the method comprises the following steps of:
    providing an internally hollow casing which has at least an inlet port of the venous blood and at least an outlet port of the arterial blood, at least an inlet channel and at least an outlet channel of a work gas intended to provide oxygen to blood and/or to remove $CO_2$ from the same, at least a flexible sheet of hollow fibres, at least a first and a second plate-shaped filtering elements of the flexible type;
    positioning said first and second filtering elements at a distance one from the other along said flexible sheet of hollow fibres;
    rolling up of said flexible sheet of hollow fibres to define a bundle of hollow fibres, said first and second filtering elements being positioned between the coils of said flexible sheet;

insertion of said bundle of hollow fibres (8) complete with said filtering elements inside said casing;

closing of said casing.

\* \* \* \* \*